United States Patent
Wagner

[19]

[11] Patent Number: 6,132,430
[45] Date of Patent: Oct. 17, 2000

[54] SPINAL FIXATION SYSTEM

[75] Inventor: Erik J. Wagner, Allen, Tex.

[73] Assignee: Spinal Concepts, Inc., Austin, Tex.

[21] Appl. No.: 09/093,756

[22] Filed: Jun. 9, 1998

Related U.S. Application Data

[62] Division of application No. 08/740,123, Oct. 24, 1996.

[51] Int. Cl.[7] ................................................... A61B 17/56
[52] U.S. Cl. ................................ 606/61; 606/72; 606/73
[58] Field of Search ........................... 606/61, 73; 623/17

[56] References Cited

U.S. PATENT DOCUMENTS

| | | |
|---|---|---|
| 4,401,112 | 8/1983 | Rezaian . |
| 4,433,677 | 2/1984 | Ulrich et al. . |
| 4,492,226 | 1/1985 | Belykh et al. . |
| 4,501,269 | 2/1985 | Bagby . |
| 4,604,995 | 8/1986 | Stephens et al. . |
| 4,641,636 | 2/1987 | Cotrel . |
| 4,743,256 | 5/1988 | Brantigan . |
| 4,763,644 | 8/1988 | Webb . |
| 4,805,602 | 2/1989 | Puno et al. . |
| 4,834,757 | 5/1989 | Brantigan . |
| 4,878,915 | 11/1989 | Brantigan . |
| 4,887,596 | 12/1989 | Sherman . |
| 4,946,458 | 8/1990 | Herma et al. . |
| 4,950,269 | 8/1990 | Gaines, Jr. . |
| 4,961,740 | 10/1990 | Ray et al. . |
| 4,987,892 | 1/1991 | Krag et al. . |
| 5,005,562 | 4/1991 | Cotrel . |
| 5,026,373 | 6/1991 | Ray et al. . |
| 5,047,029 | 9/1991 | Aebi et al. . |
| 5,055,104 | 10/1991 | Ray . |
| 5,074,864 | 12/1991 | Cozad et al. . |
| 5,102,412 | 4/1992 | Rogozinski . |
| 5,108,399 | 4/1992 | Eitenmuller et al. . |
| 5,108,446 | 4/1992 | Wagner et al. . |
| 5,123,926 | 6/1992 | Pisharodi . |
| 5,127,912 | 7/1992 | Ray et al. . |

(List continued on next page.)

FOREIGN PATENT DOCUMENTS

| | | |
|---|---|---|
| 0578320A1 | 1/1994 | European Pat. Off. . |
| 0778007A1 | 6/1997 | European Pat. Off. . |
| 0836836 | 4/1998 | European Pat. Off. . |
| 2732887A1 | 10/1996 | France . |
| 2736535A1 | 1/1997 | France . |
| 98/12976 | 4/1998 | WIPO . |

OTHER PUBLICATIONS

Wright Medical Technology Publication entitled, "Versalok Low Back Fixation System," 1996, pp. 1–4.

Danek Medical, Inc. Publication entitled, "TSRH Lumber System," 1991, pp. 1–4.

Danek Group, Inc. Medical Division Publication entitled, "TSRH Spinal System—Unmatched versatility," 1992, pp. 1–4.

Danek Surgical Technique Manual entitled, "TSRH Spinal Implant System," Date Unknown, pp. 1–16.

Danek Surgical Technique Manual entitled, "TSRH Crosslink," Date Unknown, pp. 1–8.

(List continued on next page.)

*Primary Examiner*—Michael Buiz
*Assistant Examiner*—Julian W. Woo
*Attorney, Agent, or Firm*—Conley, Rose & Tayon, PC

[57] ABSTRACT

A spinal fixation implant system for correction and fixation of the human spine to facilitate an anatomically correct fusion. The spinal fixation system may include a connector, a spinal rod, a spinal fixation component, and a fastener. The spinal fixation component preferably includes a fixation device such as a hook or screw for securing the spinal rod to vertebrae of the thoracic or lumbar spine. The connector preferably includes a threaded end adapted to receive the fastener and a receiving end adapted to receive the spinal rod. The fixation component may include a body having a tapered cavity for engaging the receiving end of the connector. Tightening of the fastener preferably draws the connector through the tapered cavity which compresses the receiving end about the spinal rod to fixably connect the spinal rod and the spinal fixation component.

106 Claims, 7 Drawing Sheets

U.S. PATENT DOCUMENTS

| | | |
|---|---|---|
| 5,129,388 | 7/1992 | Vignaud et al. |
| 5,129,904 | 7/1992 | Illi |
| 5,147,359 | 9/1992 | Cozad et al. |
| 5,154,718 | 10/1992 | Cozad et al. |
| 5,176,678 | 1/1993 | Tsou |
| 5,176,680 | 1/1993 | Vignaud et al. |
| 5,181,917 | 1/1993 | Rogozinski |
| 5,192,321 | 3/1993 | Strokon |
| 5,192,327 | 3/1993 | Brantigan et al. |
| 5,201,734 | 4/1993 | Cozad et al. |
| 5,242,445 | 9/1993 | Ashman |
| 5,246,442 | 9/1993 | Ashman et al. |
| 5,261,909 | 11/1993 | Sutterlin et al. |
| 5,263,953 | 11/1993 | Bagby |
| 5,281,222 | 1/1994 | Allard et al. |
| 5,282,801 | 2/1994 | Sherman |
| 5,290,312 | 3/1994 | Kojimoto et al. |
| 5,290,494 | 3/1994 | Coombes et al. |
| 5,303,718 | 4/1994 | Krajicek |
| 5,304,179 | 4/1994 | Wagner |
| 5,306,307 | 4/1994 | Senter et al. |
| 5,306,309 | 4/1994 | Wagner et al. |
| 5,312,405 | 5/1994 | Korotko et al. |
| 5,336,223 | 8/1994 | Rogers |
| 5,336,240 | 8/1994 | Metzler et al. |
| 5,344,422 | 9/1994 | Frigg |
| 5,348,026 | 9/1994 | Davidson |
| 5,357,983 | 10/1994 | Mathews |
| 5,360,429 | 11/1994 | Jeanson et al. |
| 5,360,431 | 11/1994 | Puno et al. |
| 5,361,766 | 11/1994 | Nichols et al. |
| 5,380,325 | 1/1995 | Lahille et al. |
| 5,390,683 | 2/1995 | Pisharodi |
| 5,397,364 | 3/1995 | Kozak et al. |
| 5,423,825 | 6/1995 | Levine |
| 5,425,772 | 6/1995 | Brantigan |
| 5,437,669 | 8/1995 | Yuan et al. |
| 5,466,237 | 11/1995 | Byrd, III et al. |
| 5,474,555 | 12/1995 | Puno et al. |
| 5,480,437 | 1/1996 | Draenert |
| 5,484,437 | 1/1996 | Michelson |
| 5,489,307 | 2/1996 | Kuslich et al. |
| 5,496,318 | 3/1996 | Howland et al. |
| 5,505,732 | 4/1996 | Michelson |
| 5,507,746 | 4/1996 | Lin |
| 5,514,180 | 5/1996 | Heggeness et al. |
| 5,520,690 | 5/1996 | Errico et al. |
| 5,522,899 | 6/1996 | Michelson |
| 5,527,341 | 6/1996 | Gogolewski et al. |
| 5,531,746 | 7/1996 | Errico et al. |
| 5,531,751 | 7/1996 | Schultheiss et al. |
| 5,536,271 | 7/1996 | Daly et al. |
| 5,545,165 | 8/1996 | Biedermann et al. |
| 5,549,608 | 8/1996 | Errico et al. |
| 5,554,157 | 9/1996 | Errico et al. |
| 5,563,124 | 10/1996 | Damien et al. |
| 5,569,246 | 10/1996 | Ojima et al. |
| 5,569,248 | 10/1996 | Matthews |
| 5,571,192 | 11/1996 | Schönhöffer |
| 5,575,792 | 11/1996 | Errico et al. |
| 5,578,033 | 11/1996 | Errico et al. |
| 5,584,834 | 12/1996 | Errico et al. |
| 5,586,984 | 12/1996 | Errico et al. |
| 5,593,409 | 1/1997 | Michelson |
| 5,601,553 | 2/1997 | Trebing et al. |
| 5,603,713 | 2/1997 | Aust et al. |
| 5,607,425 | 3/1997 | Rogozinski |
| 5,607,430 | 3/1997 | Bailey |
| 5,609,593 | 3/1997 | Errico et al. |
| 5,609,594 | 3/1997 | Errico et al. |
| 5,609,596 | 3/1997 | Pepper |
| 5,609,635 | 3/1997 | Michelson |
| 5,609,636 | 3/1997 | Kohrs et al. |
| 5,616,144 | 4/1997 | Yapp et al. |
| 5,620,443 | 4/1997 | Gertzbein et al. |
| 5,624,441 | 4/1997 | Sherman et al. |
| 5,626,579 | 5/1997 | Muschler et al. |
| 5,628,740 | 5/1997 | Mullane |
| 5,628,756 | 5/1997 | Barker, Jr. et al. |
| 5,630,816 | 5/1997 | Kambin |
| 5,632,747 | 5/1997 | Scarborough et al. |
| 5,634,925 | 6/1997 | Urbanski |
| 5,643,260 | 7/1997 | Doherty |
| 5,643,264 | 7/1997 | Sherman et al. |
| 5,643,265 | 7/1997 | Errico et al. |
| 5,645,084 | 7/1997 | McKay |
| 5,645,544 | 7/1997 | Tai et al. |
| 5,645,549 | 7/1997 | Boyd et al. |
| 5,645,598 | 7/1997 | Brosnahan, III |
| 5,647,873 | 7/1997 | Errico et al. |
| 5,649,927 | 7/1997 | Kilpela et al. |
| 5,651,283 | 7/1997 | Runciman et al. |
| 5,651,789 | 7/1997 | Cotrel |
| 5,653,708 | 8/1997 | Howland |
| 5,653,709 | 8/1997 | Frigg |
| 5,653,763 | 8/1997 | Errico et al. |
| 5,658,289 | 8/1997 | Boucher et al. |
| 5,658,337 | 8/1997 | Kohrs et al. |
| 5,658,516 | 8/1997 | Eppley et al. |
| 5,662,653 | 9/1997 | Songer et al. |
| 5,665,088 | 9/1997 | Gil et al. |
| 5,665,112 | 9/1997 | Thal |
| 5,665,122 | 9/1997 | Kambin |
| 5,667,506 | 9/1997 | Sutterlin |
| 5,667,507 | 9/1997 | Corin et al. |
| 5,667,508 | 9/1997 | Errico et al. |
| 5,668,288 | 9/1997 | Storey et al. |
| 5,669,909 | 9/1997 | Zdeblick et al. |
| 5,669,910 | 9/1997 | Korhonen et al. |
| 5,669,911 | 9/1997 | Errico et al. |
| 5,671,695 | 9/1997 | Schroeder |
| 5,672,175 | 9/1997 | Martin |
| 5,674,222 | 10/1997 | Berger et al. |
| 5,674,295 | 10/1997 | Ray et al. |
| 5,674,296 | 10/1997 | Bryan et al. |
| 5,676,665 | 10/1997 | Bryan |
| 5,676,666 | 10/1997 | Oxland et al. |
| 5,676,701 | 10/1997 | Yuan et al. |
| 5,676,703 | 10/1997 | Gelbard |
| 5,681,311 | 10/1997 | Foley et al. |
| 5,681,312 | 10/1997 | Yuan et al. |
| 5,683,391 | 11/1997 | Boyd |
| 5,683,392 | 11/1997 | Richelsoph et al. |
| 5,683,393 | 11/1997 | Ralph |
| 5,683,394 | 11/1997 | Rinner |
| 5,688,272 | 11/1997 | Montague et al. |
| 5,688,273 | 11/1997 | Errico et al. |
| 5,688,274 | 11/1997 | Errico et al. |
| 5,688,279 | 11/1997 | McNulty et al. |
| 5,688,280 | 11/1997 | Booth, Jr. et al. |
| 5,690,629 | 11/1997 | Asher et al. |
| 5,690,630 | 11/1997 | Errico et al. |
| 5,690,631 | 11/1997 | Duncan et al. |
| 5,690,632 | 11/1997 | Schwartz et al. |
| 5,690,633 | 11/1997 | Taylor et al. |
| 5,690,842 | 11/1997 | Panchison |
| 5,693,046 | 12/1997 | Songer et al. |
| 5,693,053 | 12/1997 | Estes |
| 5,693,100 | 12/1997 | Pisharodi |
| 5,697,929 | 12/1997 | Mellinger |
| 5,697,977 | 12/1997 | Pisharodi |
| 5,700,291 | 12/1997 | Kuslich et al. |

| | | |
|---|---|---|
| 5,700,292 | 12/1997 | Margulies . |
| 5,702,391 | 12/1997 | Lin . |
| 5,702,392 | 12/1997 | Wu et al. . |
| 5,702,393 | 12/1997 | Pfaifer . |
| 5,702,394 | 12/1997 | Henry et al. . |
| 5,702,395 | 12/1997 | Hopf . |
| 5,702,396 | 12/1997 | Hoenig et al. . |
| 5,702,399 | 12/1997 | Kilpela et al. . |
| 5,702,449 | 12/1997 | McKay . |
| 5,702,450 | 12/1997 | Bisserie . |
| 5,702,451 | 12/1997 | Biedermann et al. . |
| 5,702,452 | 12/1997 | Argenson et al. . |
| 5,702,453 | 12/1997 | Rabbe et al. . |
| 5,702,454 | 12/1997 | Baumgartner . |
| 5,702,455 | 12/1997 | Saggar . |
| 5,704,936 | 1/1998 | Mazel . |
| 5,704,937 | 1/1998 | Martin . |
| 5,707,372 | 1/1998 | Errico . |
| 5,707,395 | 1/1998 | Li . |
| 5,709,681 | 1/1998 | Pennig . |
| 5,709,682 | 1/1998 | Medoff . |
| 5,709,683 | 1/1998 | Bagby . |
| 5,709,684 | 1/1998 | Errico et al. . |
| 5,709,685 | 1/1998 | Dombrowski et al. . |
| 5,709,686 | 1/1998 | Talos et al. . |
| 5,713,841 | 2/1998 | Graham . |
| 5,713,898 | 2/1998 | Stucker et al. . |
| 5,713,899 | 2/1998 | Marnay et al. . |
| 5,713,900 | 2/1998 | Benzel et al. . |
| 5,713,903 | 2/1998 | Sander et al. . |
| 5,713,904 | 2/1998 | Errico et al. . |
| 5,716,355 | 2/1998 | Jackson . |
| 5,716,356 | 2/1998 | Biedermann et al. . |
| 5,716,357 | 2/1998 | Rogozinski . |
| 5,716,358 | 2/1998 | Ochoa . |
| 5,716,359 | 2/1998 | Ojima et al. . |
| 5,716,415 | 2/1998 | Steffee . |
| 5,716,416 | 2/1998 | Lin . |
| 5,720,746 | 2/1998 | Soubeiran . |
| 5,720,747 | 2/1998 | Burke . |
| 5,720,748 | 2/1998 | Kuslich et al. . |
| 5,720,751 | 2/1998 | Jackson . |
| 5,722,977 | 3/1998 | Wilhelmy . |
| 5,928,233 | 7/1999 | Apfelbaum et al. ...................... 606/61 |

OTHER PUBLICATIONS

Dickman Curtis A., et al., BNI Quarterly Publication entitled, "Techniques of Screw Fixation of the Cervical Spine," vol. 9. No. 4, Fall 1993, pp. 27–39.

Slone et al., RadioGraphics Publication entitled, "Spinal Fixation," vol. 13 No. 2, Mar. 1993, pp. 341–356.

Synthes Spine Publication entitled, "The Universal Spinal System—Internal Fixation for the Spine," 1994, pp. 1–15.

AcroMed Publication entitled, "The ISOLA Spinal System—Versatility, simplicity and minimal profile in the surgical treatment of the spine," 1994, pp. 1–15.

AcroMed Corporation Publication entitled, "ISOLA® Transverse Rod Connectors: Principles and Techniques," Date Unknown, pp. i, ii, 1–8.

Danek Publication entitled, "AXIS—Fixation System," 1993, pp. 1–6.

Synthes Publication entitled, "Small Notched Titanium Reconstruction Plate System," 1996, pp. 1–6.

J. Neurosurg Publication entitled, "Posterior plates in the management of cervical instability: long–term results in 44 patients," vol. 81, 1994, pp. 341–349.

BNI Quarterly Publication entitled, "Lateral Mass Posterior Plating and Facet Fusion for Cervical Spine Instability," vol. 7, No. 2, 1991, pp. i, ii, 1–12.

Beadling, Lee, Orthopedics Today Publication entitled, "FDA Clears Spinal Cages for Interbody Lumbar Fusion," pp. 1–2.

MedPro Month Publication entitled, "Trends in Spine & Disk Surgery," vol. VI, No. 11–12, pp. 280–284.

Surgical Dynamics Ray Threaded Fusion Cage Device Surgical Technique Manual, pp. 1–10.

Surgical Dynamics Ray Threaded Fusion Cage, pp. 1–6.

Spinal Concepts Inc. publication entitled "The BacFix ss—Posterior Lower Back Fixation System—Written Surgical Technique," 1997, pp. 1–11.

International Search Report PCT/US 97/16971 dated Feb. 6, 1998.

AcroMed Publication entitled, "AcroMed Spinal Solutions for Cervical Pathologies," Jul. 1995, pp. 1–8, printed by AcroMed Corporation 1995.

Shufflebarger, Harry L., M.D., Depuy Motech publication entitled, "Clincal Issue: Rod Rotation in Scoliosis Surgery," 5 pages.

Schufflebarger, Harry L., M.D., "Moss Miami Spinal Instrumentation System: Methods of Fixation of the Spondylopelvic Junction," *Lumbosacral and Spinopelvic Fixation*, 1996 by Raven Publishers, Philadelphia, pp. 381–393.

Depuy Motech, Inc. publication entitled, "Moss Miami 3–Dimensional Spinal Instrumentation: Taking Spinal Instrumentation to a New Dimension," 1995, 8 pp.

SPINAL FIXATION SYSTEM

This application is a division of Ser. No. 08/740,123 filed Oct. 24, 1996.

BACKGROUND OF THE INVENTION

1. Field of the Invention

The present invention generally relates to spinal fixation systems and the like. More particularly, an embodiment of the invention relates to a spinal implant system for correction, fixation, and stabilization of the human spine to allow the development of a solid spinal fusion.

2. Description of the Related Art

Spinal fixation, such as lumbar sacral fusion and the correction of spinal deformities such as scoliotic curves, is a well known and frequently used medical procedure. Pedicle, lateral, and oblique mounting devices may be used to secure corrective spinal instrumentation to a portion of the spine that has been selected to be fused by arthrodesis.

A spinal fixation system typically includes corrective spinal instrumentation that is attached to selected vertebrae of the spine by screws, hooks, and clamps. The corrective spinal instrumentation includes spinal rods or plates that are generally parallel to the patient's back. The corrective spinal instrumentation may also include transverse connecting rods that extend between neighboring spinal rods. Spinal fixation systems are used to correct problems in the lumbar and thoracic portions of the spine, and are often installed posterior to the spine on opposite sides of the spinous process and adjacent to the transverse process.

Various types of screws, hooks, and clamps have been used for attaching corrective spinal instrumentation to selected portions of the patient's spine. Examples of pedicle screws and other types of attachments are illustrated in U.S. Pat. Nos. 4,763,644; 4,805,602; 4,887,596; 4,950,269; and 5,129,388. Each of these patents is incorporated by reference as if fully set forth herein.

An eyebolt assembly of the TSRH® spinal system sold by Danek Medical Inc. is illustrated in FIG. 1. The eyebolt assembly 2 encircles spinal rod 4 such that assembly mass completely surrounds the spinal rod. The spinal rod must be inserted through the eyebolt, which rests within the yoke of spinal hook 8. The spinal hook attaches the spinal rod to a bony element of the spine. A nut 6 is threaded onto a post of the eyebolt assembly to fixably secure the rod within the yoke. The nut is tightened so that the assembly resists axial, torsional, and shear forces to inhibit motion of the spinal rod relative to the assembly in the directions indicated by the arrows in FIG. 1. Further details of the TSRH® spinal system are provided in the TSRH® Spinal Implant System Surgical Technique Manual and the TSRH® Crosslink Surgical Technique Manual. Both of these publications are available from Danek Medical Inc. and are incorporated by reference as if fully set forth herein.

Manual insertion of a spinal rod through the bores of a number of spaced-apart eyebolts within a surgical wound tends to be difficult. The bore axis of each eyebolt must be properly aligned along a common axis, which is difficult since the corrective procedure requires that the spinal rod initially be placed under stress to resist deforming forces of the spine. Therefore, the use of systems such as the TSRH® spinal system may require that a predetermined number of screws or hooks be pre-loaded onto the spinal rod in a particular order and spacing prior to the insertion of the spinal rod into the surgical wound. After insertion of the spinal system into the surgical wound, however, it is often necessary to add, delete, or reposition one or more hooks or screws. Before such modifications can be made, the spinal system typically must be removed from the surgical wound and at least partially disassembled.

To overcome such problems, some spinal fixation systems include "open back" hooks or screws to allow a spinal rod to be dropped into the open back of the hook or screw and secured within the open back by a separate component and a set screw. Such a system is illustrated in U.S. Pat. No. 5,102,412 to Rogozinski, which is incorporated by reference as if fully set forth herein. Such systems tend to be susceptible to fatigue stress failure and require assembly within the surgical wound. In addition, adding a hook or screw to the construct tends to require that the spinal rod first be repositioned. A further disadvantage of this approach is that component mass completely surrounds the spinal rod, resulting in an increase in the profile width of the device and greater impingement of the device upon the fusion mass. A low profile width is generally desired to minimize sinus formation and soft tissue irritation from hardware prominence.

U.S. Pat. No. 5,242,445 to Ashman relates to a "split eyebolt" assembly for adding eyebolts to an assembled spinal fixation construction. Attaching the split eyebolt to a spinal rod requires a special crimping tool to crimp the split eyebolt over the rod. The crimping tool tends to be difficult to operate within the surgical wound. Furthermore, the threads of the opposing sides of the split eyebolt are often misaligned after crimping, making it difficult or impossible to thread a nut onto the split eyebolt. The split eyebolt also completely encircles the spinal rod thereby increasing the impingement of the construct upon the fusion mass.

It is therefore desirable that an improved spinal fixation system be derived that facilitates assembly and surgical implantation by allowing the spinal rod to be positioned within the surgical wound (a) after the fixation components (e.g., screws, hooks) have been implanted, (b) without modifying the fixation components, and (c) whereby fixation components may be subsequently added, deleted, and/or repositioned without disassembling the system.

SUMMARY OF THE INVENTION

In accordance with the present invention, a spinal fixation system is provided that largely eliminates or reduces the aforementioned disadvantages of conventional spinal fixation constructions. An embodiment of the invention relates to an implant system for fixation of the human spine that includes a spinal rod, a fixation component, a connector, and a fastener.

The connector may be used to connect the spinal rod to the fixation component and preferably includes a receiving end and a fastening end. The receiving end may contain a first arm and a second arm that together form a substantially U-shaped borehole into which the spinal rod may be axially positioned. The receiving end preferably surrounds only part of the spinal rod such that the unsurrounded portion of the spinal rod is exposed from the borehole. The exposed portion of the spinal rod may extend out of an open end of the U-shaped borehole. The spinal rod may be circular and preferably includes a cross-section having a circumferential portion. The receiving end of the connector preferably surrounds and engages greater than about $\pi$ radians and less than about $2\pi$ radians of the circumferential portion.

The receiving end of the connector preferably acts as a "pinch clamp" by exerting a clamping force on opposing sides of the spinal rod to secure the spinal rod within the borehole. The connector preferably contains a slot between the receiving end and the fastening end that enables the first arm and the second arm to be deflected relative to one another. The deflection of the arms allows the distance between a tip of the first arm and a tip of the second arm to be changed so that the spinal rod may be inserted through an open end of the U-shaped borehole that is defined between the tips of the arms.

The fixation component preferably includes a fixation device such as a bone screw or hook for engaging vertebrae of the thoracic or lumbar spine. The fixation component also preferably includes a body containing a cavity with an inner surface. The cavity is preferably sized to receive a portion of the connector. The connector is preferably partially disposed within the cavity such that at least a portion of the fastening end extends from the cavity, whereby the inner surface of the cavity engages an outer surface of the receiving end. The cavity of the body is preferably a tapered cavity that narrows in a direction from a first end of the cavity to a second end of the cavity. The tapered cavity preferably surrounds a portion of the receiving end and imparts a compressive force against the receiving end to secure the spinal rod within the borehole.

The fastener preferably engages both the body and the portion of the fastening end that extends from the cavity. The fastener may secure the connector and the fixation component together. The fastener is preferably a nut adapted to be threaded upon the fastening end. The fastener may be selectively tightened to allow an engagement between the connector and the spinal rod that may be overcome by the application of a distraction force to the connector. Rotation of the nut in a tightening direction about the fastening end preferably draws a portion of the receiving end through the tapered cavity, causing the inner surface of the cavity to compress the arms of the receiving end. In turn, the arms may exert a compressive force against the spinal rod to clamp it within the borehole. The magnitude of the compressive force against the spinal rod preferably varies as a function of the degree to which the nut is tightened. The open end of the U-shaped borehole preferably has a width that can be adjusted by tightening the fastener.

The fixation component may include a spacer located between the fastener and the spinal rod for laterally offsetting the fixation device a selected lateral distance from the spinal rod. The spacer may include a surface having a plurality of radially-spaced teeth. The fixation component may comprise a plurality of radially-spaced protrusions adapted to fit adjacent to the teeth on the surface of the spacer. The tightening of the nut preferably causes the spacer and the fixation component to become pressed together such that a complementary engagement between the teeth of the spacer and the protrusions of the fixation device is formed to inhibit rotation of the fixation device about the spacer.

The body may include a U-shaped yoke formed between a top section and a bottom section that each have an edge adjacent to the yoke. The tapered cavity preferably is formed between the top section and the bottom section and extends in a perpendicular direction relative to the U-shaped yoke. The fixation component is preferably adapted to pivot about the spinal rod in a substantially vertical plane. The edges of the top and bottom sections preferably contact the spinal rod during the pivoting of the fixation component to define the range of pivotal motion of the fixation component about the spinal rod. The edges are preferably curved in a direction away from the spinal rod to increase the range of pivotal motion of the fixation component.

The fixation component may include a transverse connector to maintain a fixed distance between the spinal rod and a neighboring spinal rod. The transverse connector may include a reduced section that has a width less than that of the body, allowing the reduced section to be more easily bent. The reduced section may be bent to shorten the lateral distance between the spinal rod and an adjacent spinal rod. The transverse connector may contain a beveled section between the body and the reduced section.

An advantage of the present invention relates to a fixation component that may be added to or deleted from a spinal fixation construct in a surgical wound without disassembling the construct.

Another advantage of the present invention relates to a spinal fixation system requiring minimal assembly within the surgical wound.

Yet another advantage of the present invention relates to a spinal fixation system having a relatively narrow profile width to reduce impingement upon the fusion mass.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
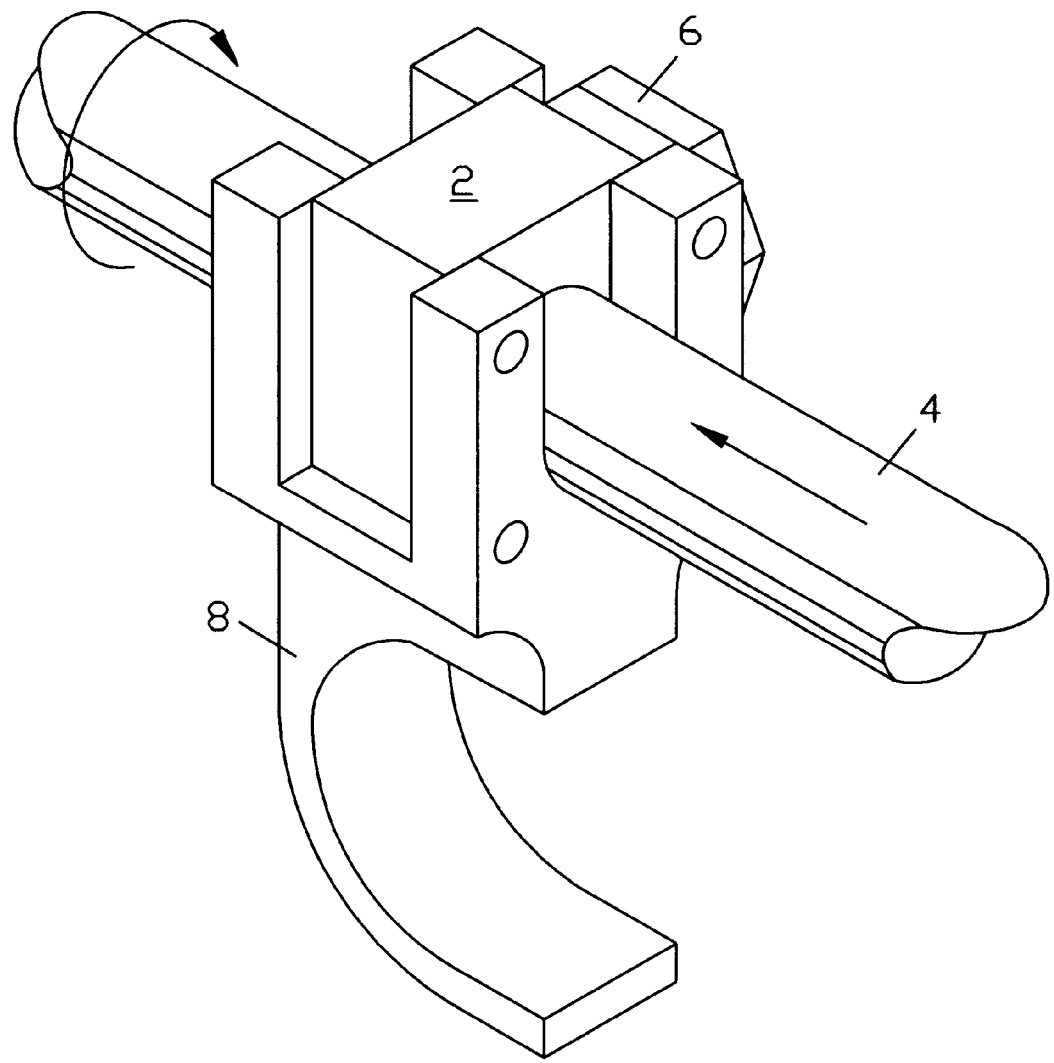
FIG. 1 depicts a TSRH® spinal system eyebolt assembly.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 2:
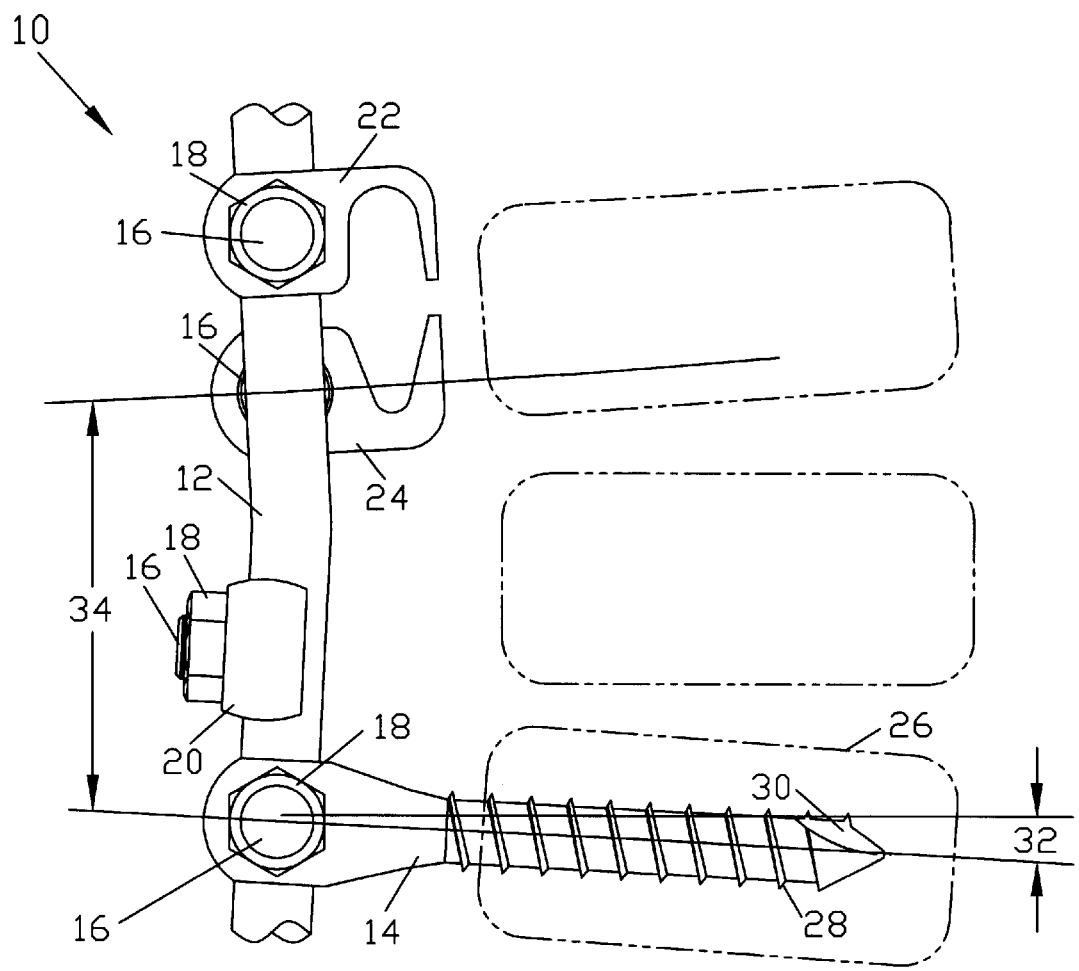
FIG. 2 depicts a side view of an embodiment of a spinal fixation system connected to a vertebra.

FIG. 2 depicts a spinal fixation system 10 constructed according to teachings of the present invention. In an embodiment of the invention, spinal fixation system 10 includes a spinal rod 12 generally aligned parallel with a portion of the spine. Connector 16 secures spinal fixation components to the spinal rod via fastener 18. The fixation components may include various fixation devices including bone screw 14, transverse connector 20, and spinal hooks 22 and 24.

Spinal rod 12 is preferably constructed of stainless steel or another relatively rigid material. The spinal rod preferably has a substantially circular cross-section (although other cross-sectional geometries may be employed) and a diameter between about ⅛ of an inch and about ¼ of an inch. The spinal rod may have a shot-peened surface to increase its resistance to fatigue failure. The spinal rod may impart forces against the spine to maintain a portion of the spine in a fixed position to correct a spinal deformity or injury. The spinal rod may be contoured to a selected shape prior to or after surgical implantation.

Bone screw 14 is preferably inserted within the main body of a vertebra 26 and may contain threads 28 to create a fixable engagement with the vertebra. Alternatively, the bone screw may have a substantially smooth shank containing no threading. The stress imparted to spinal fixation systems resulting from a spinal deformity may cause fatigue failure of a threaded bone screw if a solid spinal fusion does not develop after a period of time. Threaded screws having relatively long shanks tend to fail at a location adjacent to the screw head. A substantially smooth, unthreaded shank tends to remove the stress concentration on the screw shank from a location adjacent to the screw head where failure of the screw often occurs. The bone screw may also include a tap relief 30 to facilitate its insertion into vertebra 26. The angle of the bone screw relative to the spinal rod is preferably adjustable. The bone screw may be angled to correct the angle 32 of a vertebra relative to other vertebrae in the spine. The angle between the bone screw and spinal rod is preferably fixable by tightening fastener 18. Furthermore, the height of the vertebra 26 may be adjusted by applying a distraction force in the directions indicated by arrow 34 between a pair of fixation devices such as bone screw 14 and spinal hook 24 prior to tightening fasteners 18. The distraction force may be applied with the use of a tool in a manner well known to those skilled in the art.

The spinal hooks 22 and 24 may be any of a number of types of hooks well known to those skilled in the art including large laminar, small laminar, thoracic laminar, and pedicle hooks. Each spinal hook may be positioned in the caudal direction (illustrated by hook 24 in FIG. 2) or in the cranial direction (illustrated by hook 22 in FIG. 2). Spinal hooks may be positioned on opposing sides of the spinal rod as shown in FIG. 2.

Figure 3:
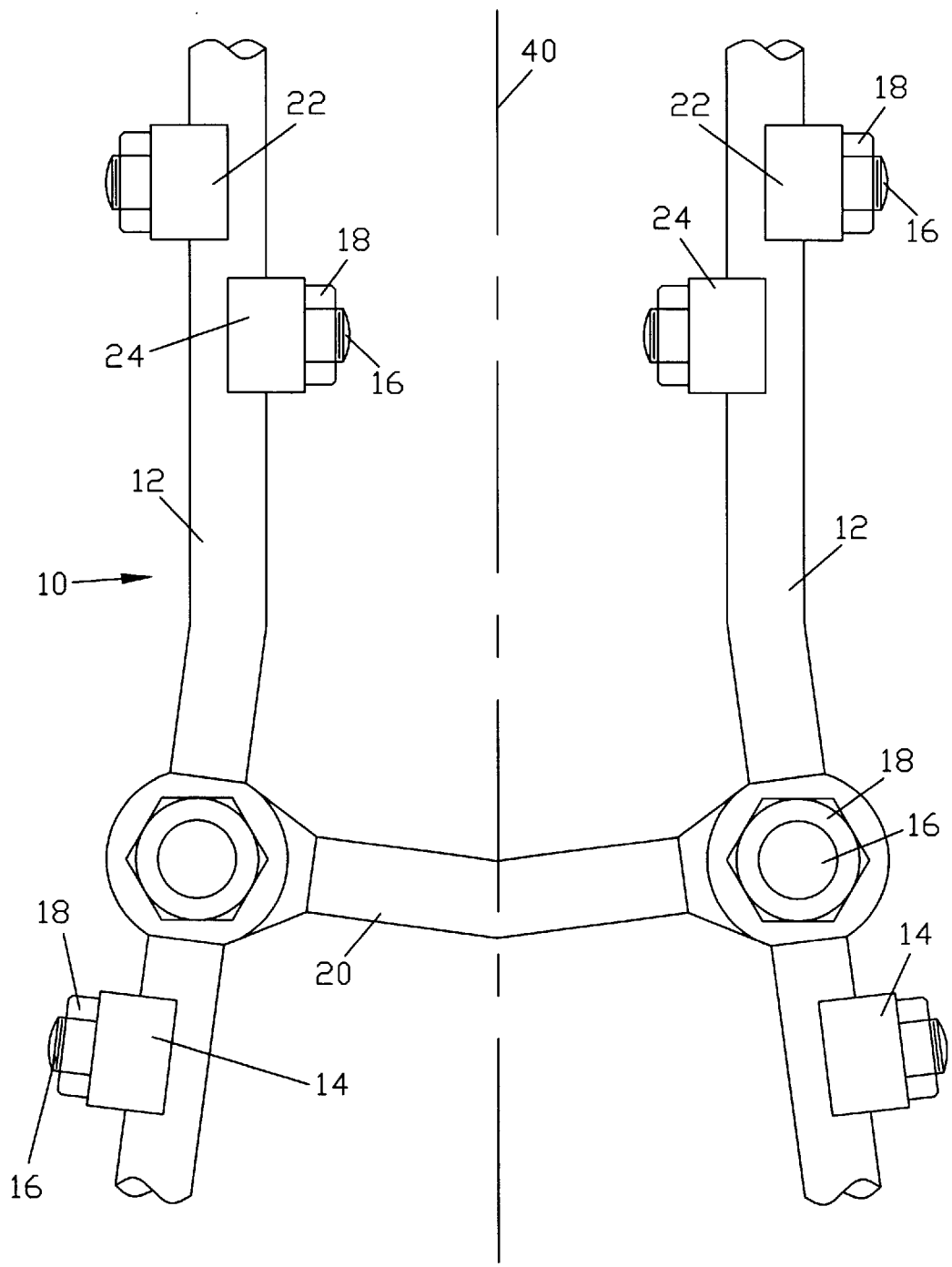
FIG. 3 depicts a top view of the spinal fixation system of FIG. 2.

FIG. 3 depicts a top view of an embodiment of spinal fixation system 10 that includes a pair of spinal rods 12 in spaced relation on each side of the vertical axis 40 of the spine. Spinal hooks 22 and 24 are preferably positioned for attachment to bony elements of the posterior human spine. One or more transverse connectors 20 may be used to rigidly link the rods to improve the strength of the assembly. Each of the fixation components may be attached to the spinal rod using a fastener 18 that engages connector 16 and the fixation component.

Transverse connector 20 may connect neighboring rods to increase the rigidity of the construct and to prevent the movement of the rods relative to one another. The transverse connector may be attached to the spinal rod using crosslinking plates that are well known to those skilled in the art and described in the TSRH® Crosslink Surgical Technique Manual, which is incorporated by reference herein. It is preferred that neighboring rods be connected by two transverse connectors that may be aligned parallel and in spaced relation from one another. If the spinal rod is bent, transverse connector 20 is preferably attached to the spinal rod at a location other than the "peak" of the curved section of the rod so that additional stress is not placed at that location.

Figure 4:
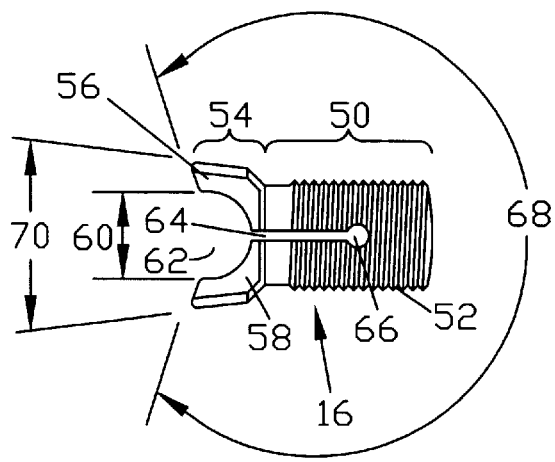
FIG. 4 depicts a side view of a tapered connector constructed in accordance with the present invention.

An embodiment of connector 16 is illustrated in FIG. 4. The connector preferably includes a fastening end 50 and a receiving end 54 opposite the fastening end. The fastening end may be a threaded end containing male machine threads 52 that are adapted to engage a fastener. The fastener is preferably a nut. The receiving end preferably includes a first arm 56 and a second arm 58 that together form a U-shaped borehole 62. The first arm has a tip 72 and the second arm has a tip 74 (each labeled in FIG. 5), and an opening 60 or open end is preferably defined by the tips of the first and second arm. A slot 64 preferably extends between the receiving end and the fastening end. The slot may extend from borehole 62 proximate the receiving end to a location proximate the fastening end. The slot may terminate in an enlarged opening 66 within the receiving end. The borehole is preferably adapted to receive a spinal rod 12 such that the first and second arms of the receiving end surround more than about half of a circumferential portion of the spinal rod.

The connector preferably does not completely surround the perimeter of the spinal rod. The unsurrounded portion of the spinal rod is preferably exposed from the open end 60 of the U-shaped borehole and may extend from the borehole through the open end. It is preferred that component mass be placed around only slightly greater than one-half of the circumference of the spinal rod to minimize the profile width of the construct. In this manner, the impingement of the construct upon the fusion mass is lessened, thereby reducing irritation of the surrounding tissue and facilitating the development of a correct spinal fusion in a minimal amount of time. Conventional assemblies tend to completely surround the spinal rod with component mass, causing a relatively greater impingement upon the fusion mass, which may interfere with fusion development.

The angle 68 in FIG. 4 is defined by the circumferential portion of a spinal rod that is surrounded by the first arm, second arm, and the end of slot 64. The angle 68 is preferably less than about 2 π radians (e.g., 360° around the cross-section of the spinal rod) and greater than about π radians (e.g., 180° around the cross-section of the spinal rod). It is preferred that more than about half of the circumferential portion the spinal rod be surrounded by a portion of the receiving end (e.g., first arm, second arm, end of slot 64) to allow the spinal rod to be adequately secured within the borehole. If less than half of the circumferential portion of the spinal rod were surrounded by the receiving end, forces resulting from spinal deformations might tend to pull the spinal rod from within borehole 62. First arm 56 and second arm 58 preferably engage the surface of greater than about half of the circumferential portion of the spinal rod.

The first arm and the second arm preferably each have an outside surface that is slightly tapered such that the distance between the outside surfaces of the arms narrows in a direction from tips 72 and 74 to the fastening end 50. The taper of the outside surfaces of the arms preferably defines a locking angle 70. Locking angle 70 is preferably a conical angle, although it may be formed within a substantially flat wedge instead. Locking angle 70 is preferably less than about 30° more preferably less than about 25°, and more preferably still between about 1° and about 20°.

Figure 5:
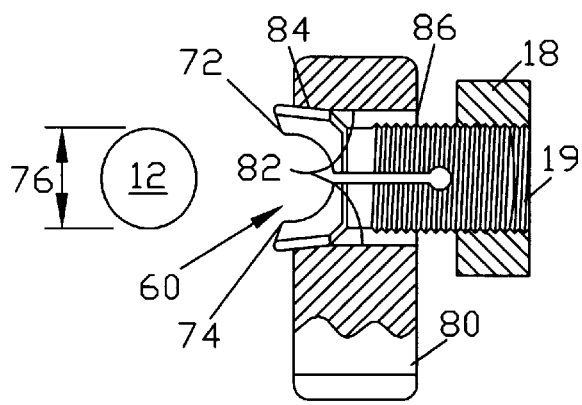
FIG. 5 depicts a side view of a tapered connector prior to assembly with a fixation component body and a spinal rod.
Figure 6:
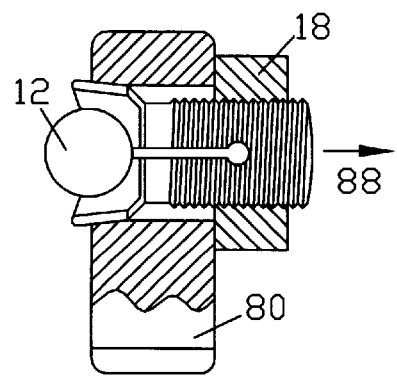
FIG. 6 depicts a side view of a tapered connector assembled with a spinal fixation component and a spinal rod.

FIGS. 5 and 6 illustrate the insertion of spinal rod 12 within borehole 62 in an embodiment of the invention. The spinal rod is preferably axially positioned within the borehole by passing the spinal rod through opening 60. Slot 64 preferably enables deflection of the first arm and the second arm relative to one another to allow the width of opening 60 to be altered. In the absence of an external force of a selected magnitude against the first or second arms, the width of opening 60 is preferably less than the outside diameter 76 of the spinal rod. Receiving end 54 is preferably adapted to form a "snap-fit" engagement with the spinal rod that may be realized by forcing the spinal rod into the inner surfaces of tips 72 and 74 of the first and second arms, respectively. The force against the inner surfaces of the tips 72 and 74 preferably causes the arms to slightly deflect in opposite directions, resulting in a slight widening of at least a portion of the slot. In this manner, the width of opening 60 may be increased by an amount sufficient to allow the insertion of the spinal rod through opening 60 and into the borehole. Once the spinal rod is fully inserted within the borehole (as shown in FIG. 6), the arms preferably move back toward one another, causing the slot to narrow to its initial, unstressed width. If the diameter of the spinal rod is slightly greater than that of the borehole, the arms may remain slightly deflected and the slot may remain slightly widened after the spinal rod is snapped into the borehole. It is generally preferred that the diameter of the spinal rod and the diameter of the borehole be equal.

In an embodiment of the invention, connector 16 connects the spinal rod to a fixation component that engages a portion of the spine. The fixation component preferably includes a fixation device such as a bone screw, hook, transverse connector, or similar device. The fixation component preferably includes a body 80 having a tapered cavity into which connector 16 may be inserted. The tapered cavity preferably tapers in a direction that is substantially perpendicular to the longitudinal axis of the fixation component. The tapered cavity preferably has a first end 84, a second end 86, and an inside surface 82. The inside surface 82 is preferably tapered at an angle that corresponds to locking angle 70. The tapered cavity preferably narrows in a direction from first end 84 to second end 86. The tapered cavity is preferably sized so that fastening end 50 and a portion of receiving end 54 may be inserted within the tapered cavity through an aperture proximate the first end. The outer width of the receiving end proximate tips 72 and 74 is preferably slightly greater than the width of the aperture proximate the first end, thereby inhibiting the complete insertion of the receiving end into the tapered cavity.

Fastener 18 may be a hex nut and preferably contains female threading 19, which is sized to fit the male machine threads of the fastening end 50. The nut preferably engages fastening end 50 and body 80 whereby rotating the fastener in a tightening direction creates a tensile force in the connector in direction 88. Tightening of the fastener preferably moves the connector within the tapered cavity in a direction from first end 84 to second end 86, thereby creating an interference fit between the arms of the receiving end and inside surface 82. As the fastener is tightened, the arms are preferably deflected toward one another such that the slot is narrowed and the arms of the receiving end exert a compressive force against the spinal rod disposed within the borehole.

The magnitude of the compressive force exerted by the receiving end on the spinal rod is preferably variable as a function of the degree to which the fastener is tightened. The fastener may be selectively tightened so that the connector is "loosely" engaged to the spinal rod. The "loose" engagement preferably fixes the position of the connector on the rod in the absence of a selected force against the connector, while allowing the connector to slide over the surface of the rod upon receiving a distraction force. For instance, the fastener may be partially tightened to loosely attach a connector and fixation device onto the rod at a selected location. A distraction force may be applied to the connector to move the connector to a selected location on the rod, and the fastener may then be fully tightened to maintain the connector at the selected location.

The arms 56 and 58 preferably exert a clamping force onto "opposite sides" of the rod (i.e., sections of the outer surface of the spinal rod that are separated by about 180°). The engagement between the arms 56 and 58 and the "opposite sides" of the spinal rod preferably "centers" the rod within the borehole as shown in FIG. 6 so that substantially no gaps exist between the inner surface of the arms and the spinal rod. The rod may be constrained on opposing sides in this manner to provide further resistance to forces that might otherwise result in axial movement of the rod. When the arms 56 and 58 are deflected to engage the spinal rod, the receiving end preferably forms a "locking taper" engagement with the spinal rod. A "locking taper" engagement is taken to mean a largely irreversible deflection of the receiving end. That is, if the fastener becomes loose after the receiving end has been compressed about the spinal rod, the clamping force exerted by the receiving end will be maintained to fixably hold the spinal rod within the borehole.

Figure 7:
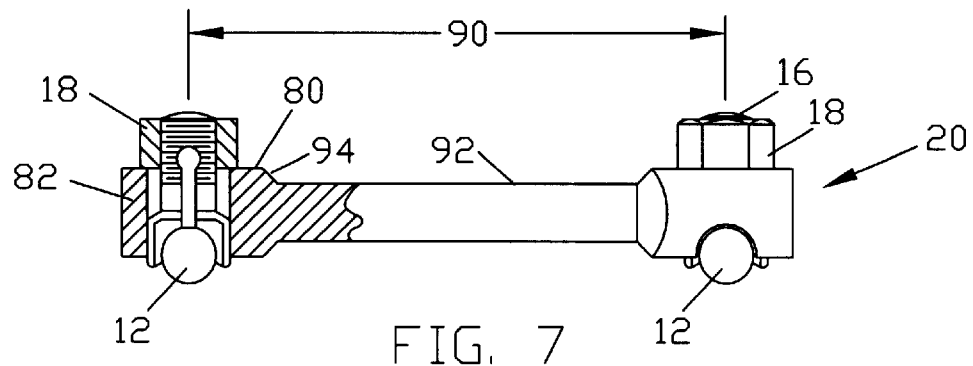
FIG. 7 depicts a side view of a transverse connector disposed between a pair of spinal rods in accordance with the present invention.

In an embodiment of the invention depicted in FIG. 7, a transverse connector 20 is disposed between a pair of spinal rods in spaced relation to secure the rods at a fixed distance 90. The spinal rods are fixed within the borehole of a connector in the manner depicted in FIGS. 5 and 6 and described above. The transverse connector may include a beveled surface between body 80 and a reduced section 92. Reduced section 92 preferably has a smaller width or diameter than body 80 to allow the reduced section to be bent more easily. Slight variations in distance 39 may be achieved by bending transverse connector 20 proximate reduced section 92. The bending of the transverse connector may be accomplished using a rod bender and a method well known to those skilled in the art. Alternately, the transverse connector may have a substantially constant width or diameter such that the width of section 92 and the width of body 80 are approximately equal.

Figure 8:
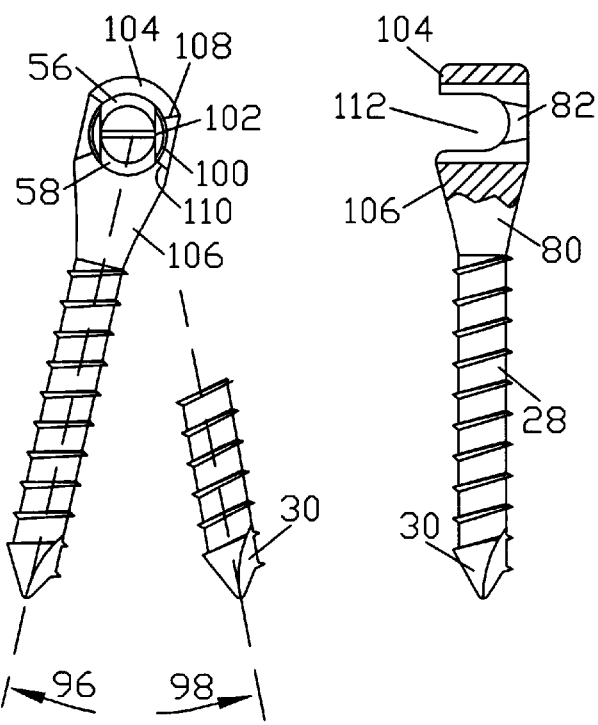
FIG. 8 depicts a front view and side view partially in section of a bone screw constructed according to teachings of the present invention.

The fixation component may include a bone screw that is used to correct the angle 32 between vertebrae. It is preferred that the bone screw be adapted to pivot about the spinal rod to form an oblique angle between the longitudinal axis of the spinal rod and the shank of the bone screw. The bone screw preferably can be pivoted in either direction 96 or direction 98 such that an oblique angle between about 90° and about 60° is formed between the shank and the longitudinal axis of the spinal rod. Other fixation devices (e.g., hooks) may be pivoted with respect the spinal rod in the same manner. As illustrated in FIG. 8, the tapered cavity may contain an engaging side 100 adapted to contact flat 102 of connector 16 to limit the pivoting of a fixation device (e.g., bone screw) about the spinal rod within a selected range, thereby preventing a gross misalignment that might complicate the assembly of the construct during a surgical procedure.

Body 80 preferably includes a top section 104 and a bottom section 106 that together form a U-shaped yoke 112 that is substantially perpendicular to inside surface 82 of the tapered cavity. The fixation component may pivot about the spinal rod. The edges of top section 104 and/or bottom section 106 may contact the spinal rod to prevent the pivoting of the fixation component about the spinal rod beyond a selected degree. Top section 104 preferably contains a curved edge 108, and bottom section 106 preferably contains a curved edge 110. Curved edges 108 and 110 preferably increase the degree that the fixation component can pivot and allow a fixation device (e.g., bone screw 14) to form an angle within a selected range that is perpendicular with or oblique to the spinal rod.

In an embodiment of the invention, body 80 is laterally offset from the spinal rod. Body 80 may contain a spacer 114 that extends laterally to offset a fixation component from the spinal rod. Offsetting a fixation component from the spinal rod may reduce the degree that the spinal rod must be contoured for proper positioning of bone screws (e.g., pedicle screws) in regions of the spine such as the lower lumbar region. The offset between the fixation component and the spinal rod may be equal to the width of the spacer. The offset is preferably less than about 15 mm, more preferably less than about 10 mm, and more preferably still between about 3 mm and about 9 mm.

Figure 9:
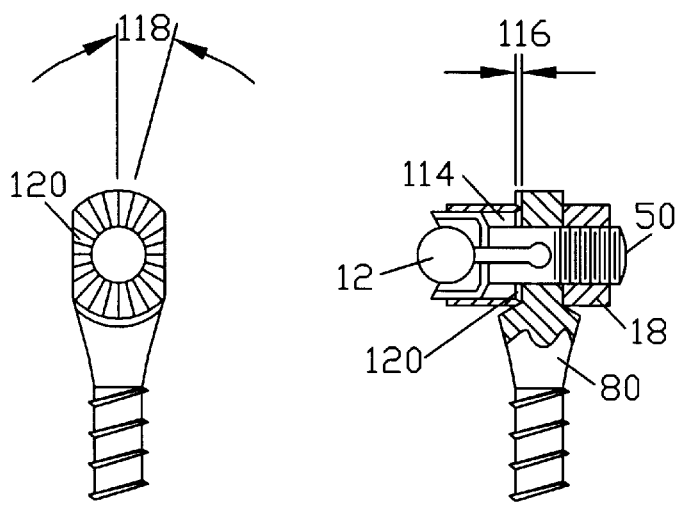
FIG. 9 depicts a front view and side view partially in section of a bone screw having radially-spaced protrusions in accordance with the present invention.

The spacer may contain a tapered cavity for receiving connector 16 as illustrated in FIG. 9. In an embodiment, the spacer contains a first plurality of protrusions or teeth that are adapted to form an engagement with a second plurality of protrusions or teeth 120 disposed on a surface of a fixation device. The teeth of the spacer and the teeth of the fixation device preferably are radially spaced at a fixed spacing 118. The teeth of the spacer and the protrusions of the fixation device preferably form a complementary fit such that adjacent, opposing teeth contact one another over interface length 116 when fastener 18 is tightened. The complementary engagement of the teeth preferably inhibits and/or prevents the fixation device from rotating about spacer 114, thereby fixing the angle formed between the fixation device and the spinal rod.

Figure 10C:
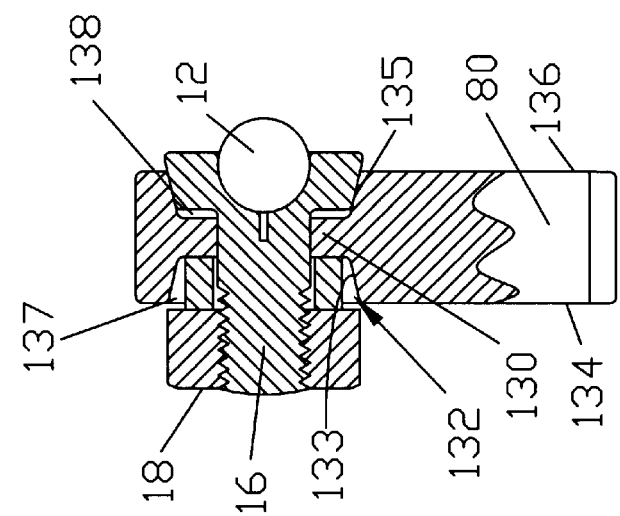
FIG. 10 depicts a front view and a side view partially in section of a reversible fixation component constructed according to teachings or the present invention.
Figure 10B:
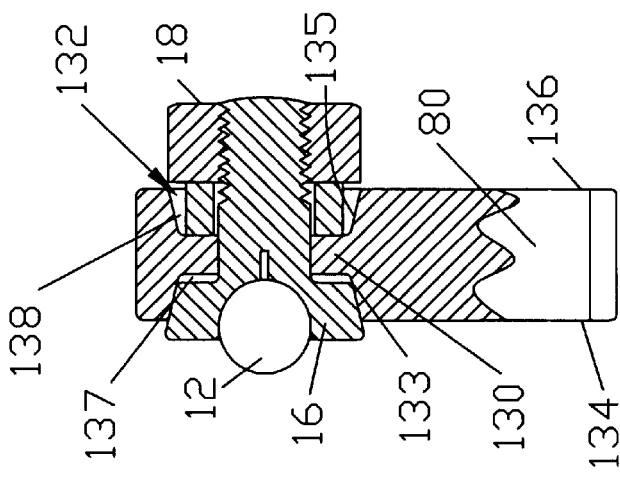
Figure 10A:
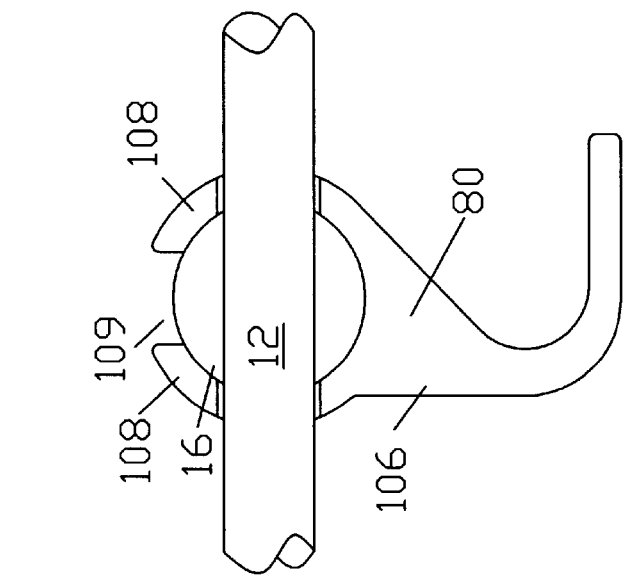

An embodiment including a reversible fixation device is illustrated in FIG. 10. The body 80 of the hook preferably includes a first U-shaped yoke 137 disposed on a first side 134 of the body and a second U-shaped yoke 138 disposed on a second side 136 of the body. A cavity 132 preferably extends through the body from the first side 134 to the second side 136. The cavity preferably contains a pair of tapered inner surfaces 133 and 135 that taper in opposite directions such that the cavity narrows in a direction from the first side 134 to the middle of the cavity and narrows in a direction from the second side 136 to the middle of the cavity. The tapered inner surfaces preferably each terminate in an engaging portion 130 disposed in the middle of the cavity. Connector 16 may be positioned within the cavity so that the receiving end extends from either first side 134 as shown in FIG. 10B or from second side 136 as shown in FIG. 10C. Thus, the reversible hook may be mounted so that either first side 134 or second side 136 is proximate the spinal rod, with the hook directed toward either the caudal or cranial direction in each case. The fixation component may contain a slot 109 through which the fastening end of the connector may be inserted during assembly of the construct. The engaging portion 130 preferably engages the outer surface of the receiving end to limit the extent to which the receiving end may be inserted into cavity 132. Fastener 18 preferably engages body 80 proximate the engaging portion.

Figure 11:
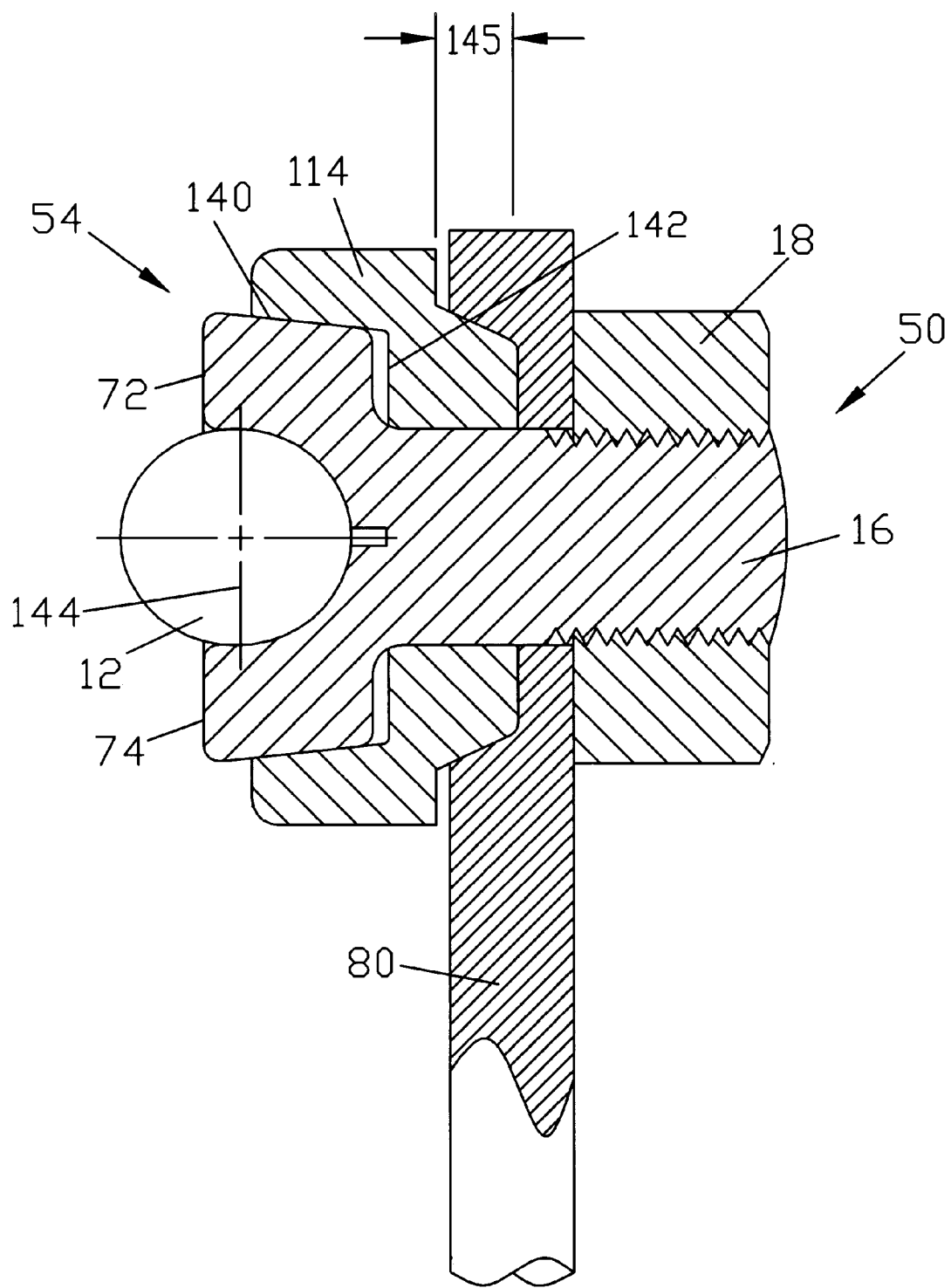
FIG. 11 depicts a side view partially in section of a spacer disposed between a spinal rod and a fastener in accordance with the present invention.

An alternate embodiment including a spacer 114 is illustrated in FIG. 11. The spacer preferably surrounds a portion of connector 16 and contains a tapered surface 140 corresponding to the outside surface of the arms of the receiving end. As fastener 18 is tightened, the connector is preferably drawn within the spacer whereby surface 140 engages and exerts a clamping force against the outer surface of the receiving end. A tensile force created by the tightening of fastener 18 preferably maintains the spacer in a fixed position between body 80 and the spinal rod. The tapered surface 140 may terminate in an engaging surface 142 that engages the receiving end, thereby limiting the extent to which the receiving end may be drawn within the spacer. The receiving end preferably forms a "pinch clamp" about the spinal rod, wherein the tips 72 and 74 of the arms terminate slightly beyond a vertical axis 144, which extends through the center of the spinal rod. The fastener may be fully tightened to create a selected offset length 145 that is preferably between about 2 mm and about 10 mm.

To surgically install spinal fixation system 10, the threaded end of connector 16 is preferably inserted through the tapered cavity of a spinal fixation component and fastener 18 is loosely threaded onto the threaded end. The spinal fixation component is then attached to the spine via a hook or screw in a selected location. A plurality of spinal fixation components may be attached to the spine in like manner. Spinal rod 11 may be contoured to match the desired curvature of the spine and placed into the surgical opening. The spinal rod is preferably snapped within the borehole of the connector of each spinal fixation component. The spine is preferably manipulated such that each of the vertebra is at a selected angle and height relative to neighboring vertebrae and then each fastener 18 is fully tightened to fixably secure the spinal rod into the borehole of each connector and to secure each of the spinal fixation devices at a selected angle relative to the spinal rod. It is generally preferred that the only assembly of system components that occurs within the surgical wound is (a) the snapping of the spinal rod within one or more connectors and (b) the final tightening of one or more fasteners that have already been engaged with the fastening end. Each of the fasteners is preferably tightened with a torque of at least 150 lb-in. One or more transverse connectors may be added across neighboring spinal rods for support to increase the strength of the overall construct and maintain the spinal rods at a fixed distance from one another.

In an alternate embodiment, each connector and spinal fixation component can be preassembled on the spinal rod prior to the implantation of the rod into the surgical wound. A connector may first be snapped onto the spinal rod. A fixation component may be added onto the connector such that the fastening end of the connector extends through the tapered cavity and the arms of the receiving end contact the inner surface of the tapered cavity. The fastener is preferably positioned on the fastening end and partially tightened to maintain the connector and fixation component engaged with the spinal rod. The fastener is preferably loosely secured on the fastening end to allow the connector and fixation component to slide along the length of the rod when a selected force is applied to the connector. The spinal rod may be contoured as necessary, and the pre-assembled system may be inserted within the surgical wound. The location of the spinal fixation components may be adjusted along the length of the rod as necessary, and the construct may be connected to the spine via fixation devices. Once a fixation component is placed at a selected location, its corresponding fastener may be fully tightened to fix its location. Fixation components may be added to or deleted from the construct as necessary without altering the position of the spinal rod or other fixation components.

In an alternate embodiment, the system may be partially pre-assembled such that a number of connectors are initially snapped onto the spinal rod. Fixation components may be inserted within the surgical wound and connected to the spine at selected locations via fixation devices. The rod may be selectively contoured and inserted within the surgical wound and aligned proximate the spine. A connector is preferably slid along the rod to a selected location proximate a fixation component on the spine, and the fastening end of the connector is inserted through the tapered cavity of the fixation component. A fastener may be placed on the fastening end to clamp the connector onto the spinal rod and to secure the fixation component therebetween. Additional connectors and fixation components may be secured to the spinal rod in like manner.

After the rod is implanted into the surgical wound, it may be necessary to add or delete a fixation component. Conventional systems tend to require that the spinal rod be removed from the surgical wound to allow a fixation component to be threaded onto or removed from the rod. In addition, fixation components of conventional systems may have to be removed from the construct to slide the added fixation component to a selected position. Connector 16 is preferably snapped onto the spinal rod at a selected location. Thus, a connector and any fixation device (e.g., screw, hook, transverse connector) may be added to the spinal rod without removing fixation components from the spinal rod or removing the spinal rod from the surgical wound. In the same manner, a connector and fixation device may be removed from the spinal rod without altering the position of the spinal rod or adjacent connectors. The fastener 18 may be loosened and a tool may be used to unclamp the receiving end of the connector from the spinal rod, thereby eliminating the need to slide the component off the end of the spinal rod as in some conventional systems.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A connector for connecting spinal fixation components to a spinal rod, comprising
   a threaded end;
   a receiving end opposite the threaded end, the receiving end terminating in a first arm and a second arm that together form a substantially U-shaped borehole for receiving the spinal rod, the first arm comprising a first tip and the second arm comprising a second tip, and wherein the borehole comprises an open end having a width defined by the first tip and the second tip; and
   a slot extending between the threaded end and the receiving end;
   and wherein the arms are deflectable to cause narrowing or widening of a portion of the slot and variation of the width of the open end to allow the spinal rod to be snapped into the borehole through the open end to form a fixable engagement between the spinal rod and the receiving end.

2. The connector of claim 1 wherein the connector is adapted to fixably hold the spinal rod within the borehole such that a portion of the spinal rod is exposed from the receiving end.

3. The connector of claim 1 wherein the spinal rod comprises a circumferential portion consisting of $2\pi$ radians, and wherein the receiving end is adapted to engage greater than about $\pi$ radians and less than about $2\pi$ radians of the circumferential portion.

4. The connector of claim 1 wherein the first and second arms are deflectable to form a locking taper engagement with the spinal rod.

5. The connector of claim 1 wherein the first and second arms each have a tapered outer surface that is angled toward the threaded end.

6. The connector of claim 1 wherein the connector is adapted to fixably hold the spinal rod within the borehole such that a portion of the spinal rod is exposed from the receiving end, and wherein the exposed portion extends from the borehole through the open end.

7. A connecting device for a spinal implant system comprising:
   a connector comprising a fastening end and a receiving end opposite the fastening end, the receiving end terminating in a first arm and a second arm that together form a substantially U-shaped borehole; and
   a body comprising a tapered cavity having an inner surface, the tapered cavity comprising a first end and a second end narrowing in a direction from the first end to the second end;
   and wherein the connector is adapted to being drawn into the tapered cavity such that the inner surface of the tapered cavity engages the receiving end and exerts a compressive force on the receiving end, thereby causing the receiving end to exert a clamping force on a spinal rod.

8. A connector for connecting a spinal fixation component to a spinal rod comprising:
   an opposing pair of deflectable arms;
   a member attached to the arms and extending away from the arms, wherein the member is configured to extend through an opening in a spinal fixation component during use; and
   wherein the arms define an open-sided borehole, and further wherein the arms are configured to snap lock to a spinal rod and to surround more than half, but less than the complete circumference of a spinal rod in the snap-locked position, such that the connector is slidable along the length of a spinal rod while the spinal rod and connector are engaged in the snap-locked position, and further wherein the arms are configured to be compressible against the spinal rod when the connector is fixed to a spinal fixation component.

9. The connector of claim 8, wherein the arms define an arcuate, open-sided borehole.

10. The connector of claim 8, wherein the member is comprises a threaded projection.

11. The connector of claim 8, wherein the member comprises a collapsible slot extending to the borehole, wherein compressing the slot decreases the size of the borehole, effective to press and lock the arms against a spinal rod during use.

12. The connector of claim 8, wherein the arms are configured to be disposed within a tapered cavity so that movement of the arms into the cavity forces the arms together.

13. The connector of claim 8 wherein the arms each have a tapered outer surface that is angled toward the member.

14. The connector of claim 8, connected to a spinal fixation component.

15. The connector of claim 14, wherein the spinal fixation component is a bone screw.

16. The connector of claim 14, wherein the spinal fixation component is a spinal hook.

17. A connector for connecting a spinal fixation component to a spinal rod comprising:

an opposing pair of deflectable arms configured to define an open-sided borehole;

a member attached to the arms and extending away from the arms, wherein the member is configured to extend through an opening in a spinal fixation component during use; and an opposing pair of deflectable arms configured to define an open-sided borehole;

a member attached to the arms and extending away from the arms, wherein the member is configured to extend through an opening in a spinal fixation component during use; and wherein the member comprises a slot extending from the borehole into the member, and wherein the arms are configured to be pressed during use against a spinal rod disposed in the borehole when a compressing force is applied to the member or to the arms.

18. The connector of claim 17, wherein the arms are configured to snap lock to a spinal rod and to surround more than half, but less than the complete circumference of a spinal rod in the snap-locked position, such that the connector is slidable along the length of a spinal rod while the spinal rod and connector are engaged in the snap-locked position.

19. The connector of claim 18 wherein the arms each have a tapered outer surface that is angled toward the member.

20. The connector of claim 19, connected to a spinal fixation component.

21. The connector of claim 20, wherein the spinal fixation component is a bone screw.

22. The connector of claim 20, wherein the spinal fixation component is a spinal hook.

23. A connector for connecting a spinal fixation component to a spinal rod comprising:

an opposing pair of deflectable arms, each comprising a tapered outer surface that is angled toward an attached member;

a member attached to the arms and extending away from the arms, wherein the member is configured to project through an opening in a spinal fixation component during use; and wherein the arms define an open-sided borehole, and further wherein the arms are configured to snap lock to a spinal rod and to surround more than half, but less than the complete circumference of a spinal rod in the snap-locked position, such that the connector is slidable along the length of a spinal rod while the spinal rod and connector are engaged in the snap-locked position, and further wherein the arms are configured to be compressible against the spinal rod when the connector is fixed to a spinal fixation component.

24. The connector of claim 22, wherein the member is threaded.

25. An implant system for fixation of the human spine, comprising:

a connector comprising a receiving end and a fastening end, the receiving end forming a substantially U-shaped opening;

a spinal rod axially positionable within the opening so that a circumferential portion of the spinal rod is exposed from the opening, the spinal rod being fixable within the opening by a clamping force exerted by the connector during use;

a fixation component comprising a body, a fixation device having protrusions, and a spacer having teeth;

a cavity in the body, the cavity comprising an inner surface, wherein the connector is configured to be at least partially disposed within the cavity during use such that the inner surface of the cavity engages an outer surface of the receiving end; and a fastener configured to engage the body and the connector to secure the connector and the fixation component together during use;

wherein the fixation device and the spacer are configured to fit between the fastener and the spinal rod, and wherein the teeth of the spacer engage the protrusions of the fixation device to inhibit rotation of the fixation device about the spacer during use.

26. The implant system of claim 25, wherein the receiving end comprises a first arm having a first tip, and a second arm having a second tip, wherein the substantially U-shaped opening is formed between said first arm and said second arm.

27. The implant system of claim 26, further comprising a slot in the connector between the receiving end and the fastening end, the slot enabling the first arm and the second arm to deflect relative to one another and change a distance between the first tip and the second tip.

28. The implant system of claim 25, wherein the fastener is a threaded nut and the fastening end comprises threading adapted to engage the nut.

29. The implant system of claim 28, wherein tightening the nut along the fastening end causes movement of the receiving end within the cavity whereby the inner surface of the cavity exerts a compressive force against an outer surface of the receiving end that compresses the U-shaped opening.

30. The implant system of claim 25, wherein greater than about $\pi$ radians and less than about $2\pi$ radians of the circumferential portion is engaged by the receiving end.

31. The implant system of claim 25, wherein the body comprises a substantially U-shaped yoke having an axial length, the yoke being formed between a top section and a bottom section, the top section comprising a first edge, the bottom section comprising a second edge, the first and second edges defining a width of the yoke, and wherein the first and second edges are curved such that the width of the yoke varies across the axial length of the yoke.

32. The implant system of claim 25, wherein the spacer has a width between about 1 mm and about 10 mm and wherein the spacer is disposed between the fastener and the spinal rod to laterally offset the fixation device from the spinal rod.

33. The implant system of claim 25, wherein the fixation component further comprises a transverse connector for connecting the spinal rod to a neighboring spinal rod, the transverse connector comprising a reduced section and a beveled section, the reduced section having a width less than a width of the body, the beveled section being located between the body and the reduced section.

34. The implant system of claim 25, wherein the cavity of the body is a tapered cavity having a first end and a second end, and wherein the tapered cavity narrows in a direction from the first end to the second end.

35. The implant system of claim 34, wherein the tapered cavity is adapted to substantially surround a portion of the receiving end and impart a compressive force against the receiving end to fixably secure the spinal rod within the opening.

36. The implant system of claim 25, wherein the fixation component further comprises a fixation device for attaching the spinal rod to a vertebra.

37. The implant system of claim 25, wherein the body further comprises a top section and a bottom section, the cavity being formed in between the top section and the bottom section, the top section and the bottom section each comprising edges that are curved, and wherein the fixation component is adapted to pivot about the spinal rod in a substantially vertical plane, and wherein the curved edges are adapted to contact the spinal rod during the pivoting of the fixation component, thereby defining a range of pivotal motion of the fixation component.

38. The implant system of claim 25, wherein the connector is adapted to be at least partially disposed within the cavity such that at least a portion of the fastening end extends from the cavity.

39. An implant system for fixation of the human spine, comprising:
   a connector comprising a receiving end and a fastening end, the receiving end forming a substantially U-shaped opening;
   a spinal rod axially positionable within the opening so that a circumferential portion of the spinal rod is exposed from the opening, the spinal rod being fixable within the opening by a clamping force exerted by the connector during use;
   a fixation component comprising a body, the body comprising a top section having curved edges, a bottom section having curved edges, and a cavity having an inner surface, the cavity formed between the top section and the bottom section; and
   a fastener configured to engage the body and the connector to secure the connector and the fixation component together during use;
   wherein the fixation component is configured to pivot about the spinal rod in a substantially vertical plane, and wherein the curved edges of the top section and the bottom section are configured to contact the spinal rod during the pivoting of the fixation component, thereby defining a range of pivotal motion of the fixation component.

40. The implant system of claim 39, wherein the receiving end comprises a first arm having a first tip, and a second arm having a second tip, wherein the substantially U-shaped opening is formed between said first arm and said second arm.

41. The implant system of claim 40, further comprising a slot in the connector between the receiving end and the fastening end, the slot enabling the first arm and the second arm to deflect relative to one another and change a distance between the first tip and the second tip.

42. The implant system of claim 39, wherein the fastener is a threaded nut and the fastening end comprises threading adapted to engage the nut.

43. The implant system of claim 42, wherein tightening the nut along the fastening end causes movement of the receiving end within the cavity whereby the inner surface of the cavity exerts a compressive force against an outer surface of the receiving end that compresses the U-shaped opening.

44. The implant system of claim 39, wherein greater than about π radians and less than about 2 π radians of the circumferential portion is engaged by the receiving end.

45. The implant system of claim 39, wherein the body comprises a substantially U-shaped yoke having an axial length, the yoke being formed between a top section and a bottom section, the top section comprising a first edge, the bottom section comprising a second edge, the first and second edges defining a width of the yoke, and wherein the first and second edges are curved such that the width of the yoke varies across the axial length of the yoke.

46. The implant system of claim 39, wherein the fixation component further comprises a fixation device and a spacer, the fixation device extending from the body, the spacer having a width between about 1 mm and about 10 mm, and wherein the spacer is disposed between the fastener and the spinal rod to laterally offset the fixation device from the spinal rod.

47. The implant system of claim 39, wherein the fixation component further comprises a transverse connector for connecting the spinal rod to a neighboring spinal rod, the transverse connector comprising a reduced section and a beveled section, the reduced section having a width less than a width of the body, the beveled section being located between the body and the reduced section.

48. The implant system of claim 39, wherein the cavity of the body is a tapered cavity having a first end and a second end, and wherein the tapered cavity narrows in a direction from the first end to the second end.

49. The implant system of claim 48, wherein the tapered cavity is adapted to substantially surround a portion of the receiving end and impart a compressive force against the receiving end to fixably secure the spinal rod within the opening.

50. The implant system of claim 39, wherein the fixation component further comprises a fixation device for attaching the spinal rod to a vertebra.

51. The implant system of claim 39, wherein the fixation component further comprises a fixation device and a spacer adapted to fit between the fastener and the spinal rod, the fixation device comprising protrusions, the spacer offsetting the fixation device from the spinal rod and comprising teeth adapted to form a complementary engagement with the protrusions to inhibit rotation of the fixation device about the spacer.

52. The implant system of claim 39, wherein the connector is adapted to be at least partially disposed within the cavity such that at least a portion of the fastening end extends from the cavity.

53. An implant system for fixation of the human spine, comprising:
   a connector comprising a receiving end and a fastening end, the receiving end forming a substantially U-shaped opening;
   a spinal rod axially positionable within the opening so that a circumferential portion of the spinal rod is exposed from the opening, the spinal rod being fixable within the opening by a clamping force exerted by the connector during use;
   a fixation component comprising a body, the body comprising a cavity having an inner surface, and wherein the connector is configured to be at least partially disposed within the cavity such that the inner surface of the cavity engages an outer surface of the receiving end;
   a fastener configured to engage the body and the connector to secure the connector and the fixation component together during use; and
   a transverse connector configured to connect the spinal rod to a neighboring spinal rod, the transverse connector comprising a reduced section and a beveled section, the reduced section having a width less than a width of the body, the beveled section being located between the body and the reduced section;

wherein the reduced section comprises a bend to shorten a lateral distance between the spinal rod and the neighboring spinal rod.

54. The implant system of claim 53, wherein the receiving end comprises a first arm having a first tip, and a second arm having a second tip, wherein the substantially U-shaped opening is formed between said first arm and said second arm.

55. The implant system of claim 54, further comprising a slot in the connector between the receiving end and the fastening end, the slot enabling the first arm and the second arm to deflect relative to one another and change a distance between the first tip and the second tip.

56. The implant system of claim 53, wherein the fastener is a threaded nut and the fastening end comprises threading adapted to engage the nut.

57. The implant system of claim 56, wherein tightening the nut along the fastening end causes movement of the receiving end within the cavity whereby the inner surface of the cavity exerts a compressive force against an outer surface of the receiving end that compresses the U-shaped opening.

58. The implant system of claim 53, wherein greater than about $\pi$ radians and less than about $2\pi$ radians of the circumferential portion is engaged by the receiving end.

59. The implant system of claim 53, wherein the body comprises a substantially U-shaped yoke having an axial length, the yoke being formed between a top section and a bottom section, the top section comprising a first edge, the bottom section comprising a second edge, the first and second edges defining a width of the yoke, and wherein the first and second edges are curved such that the width of the yoke varies across the axial length of the yoke.

60. The implant system of claim 53, wherein the fixation component further comprises a fixation device and a spacer, the fixation device extending from the body, the spacer having a width between about 1 mm and about 10 mm, and wherein the spacer is disposed between the fastener and the spinal rod to laterally offset the fixation device from the spinal rod.

61. The implant system of claim 53, wherein the body further comprises a top section and a bottom section, the cavity being formed in between the top section and the bottom section, the top section and the bottom section each comprising edges that are curved, and wherein the fixation component is adapted to pivot about the spinal rod in a substantially vertical plane, and wherein the curved edges are adapted to contact the spinal rod during the pivoting of the fixation component, thereby defining a range of pivotal motion of the fixation component.

62. The implant system of claim 53, wherein the cavity of the body is a tapered cavity having a first end and a second end, and wherein the tapered cavity narrows in a direction from the first end to the second end.

63. The implant system of claim 62, wherein the tapered cavity is adapted to substantially surround a portion of the receiving end and impart a compressive force against the receiving end to fixably secure the spinal rod within the opening.

64. The implant system of claim 53, wherein the fixation component further comprises a fixation device for attaching the spinal rod to a vertebra.

65. The implant system of claim 53, wherein the fixation component further comprises a fixation device and a spacer adapted to fit between the fastener and the spinal rod, the fixation device comprising protrusions, the spacer offsetting the fixation device from the spinal rod and comprising teeth adapted to form a complementary engagement with the protrusions to inhibit rotation of the fixation device about the spacer.

66. The implant system of claim 53, wherein the connector is adapted to be at least partially disposed within the cavity such that at least a portion of the fastening end extends from the cavity.

67. An implant system for fixation of the human spine, comprising:

a connector comprising a threaded end, a receiving end opposite the threaded end, the receiving end terminating in a first arm and a second arm that together form a substantially U-shaped opening, the first arm comprising a first tip and the second arm comprising a second tip;

a spinal rod axially positionable between the first and the second arm;

a fixation component comprising a body, the body comprising a tapered cavity having an inner surface, the tapered cavity being adapted to receive the connector such that the inner surface engages the first arm and the second arm;

a fastener adapted to engage the threaded end of the connector and the body of the fixation component, and wherein the fastener is adapted to being moved along the threaded end to cause movement of the receiving end within the tapered cavity and deflection of the first and second arms such that the first and second arms exert a compressive force against the spinal rod to maintain the spinal rod within the opening.

68. The implant system of claim 67, wherein the spinal rod comprises a diameter, and wherein the opening has a width defined by the first tip and the second tip, and wherein the width is adjustable by rotating the fastener about the threaded end.

69. The implant system of claim 67, wherein the first and second arms are deflectable in a direction toward one another and in a direction away from one another.

70. The implant system of claim 67, wherein the spinal rod is positioned within the opening and wherein a portion of the spinal rod is exposed from the receiving end of the connector in a direction away from the threaded end.

71. The implant system of claim 67, wherein the connector further comprises a slot between the receiving end and the fastening end, and wherein the fastener is adapted to be tightened to move the connector within the tapered cavity in a direction from a first end of the tapered cavity to a second end of the tapered cavity, the tapered cavity being narrower at a location proximate the second end than at a location proximate the first end, and wherein contact between the tapered cavity and the receiving end causes deflection of the first arm and the second arm such that a portion of the slot narrows and the arms exert a compressive force against the spinal rod to clamp the spinal rod within the opening.

72. The implant system of claim 67, wherein the spinal rod comprises a cross-section having a circumferential portion, and wherein between about $\pi$ radians and about $2\pi$ radians of the circumferential portion is surrounded by the receiving end.

73. The implant system of claim 67, wherein the fixation component further comprises a bone screw having a shank with a threaded portion and a tap relief.

74. The implant system of claim 67, wherein the fixation component further comprises a bone screw having a substantially smooth, unthreaded shank.

75. The implant system of claim 67, wherein the fixation component further comprises a transverse connector for connecting the spinal rod to a neighboring spinal rod at a fixed distance.

76. The implant system of claim 67, wherein the body comprises a substantially U-shaped yoke having an axial length, the yoke being formed between a top section and a bottom section, the top section comprising a first edge, the bottom section comprising a second edge, the first and second edges defining a width of the yoke, and wherein the first and second edges are curved such that the width of the yoke varies across the axial length of the yoke.

77. The implant system of claim 67, wherein the fixation component further comprises a fixation device and a spacer adapted to fit between the fastener and the spinal rod to laterally offset the fixation device from the spinal rod.

78. The implant system of claim 67, wherein the fixation component further comprises a fixation device and a spacer, the spacer being adapted to fit between the fastener and the spinal rod, the fixation device comprising protrusions, the spacer being adapted to offset the fixation device from the spinal rod and comprising teeth adapted to form a complementary engagement with the protrusions to inhibit rotation of the fixation device about the spacer.

79. The implant system of claim 67, wherein the body further comprises a top section and a bottom section, the tapered cavity being formed in between the top section and the bottom section, the top section and the bottom section each comprising edges that are curved in a direction away from the spinal rod.

80. The implant system of claim 67, wherein the fixation component further comprises a fixation device and a spacer, the fixation device extending from the body, the spacer having a width between about 1 mm and about 10 mm and being adapted to fit between the fastener and the spinal rod to laterally offset the fixation device from the spinal rod.

81. The implant system of claim 67, wherein the compressive force exerted against the spinal rod is selectively variable and is a function of a position of the fastener on the threaded end.

82. The implant system of claim 67, wherein the fixation component further comprises a transverse connector connecting the spinal rod to a neighboring spinal rod, the transverse connector comprising a reduced section and a beveled section, the reduced section having a width less than a width of the body, the beveled section connecting the reduced section to the body.

83. The implant system of claim 67, wherein the fixation component further comprises a transverse connector connecting the spinal rod to a neighboring spinal rod, the transverse connector comprising a reduced section and a beveled section, the reduced section having a width less than a width of the body, the beveled section extending between the body and the reduced section, and wherein the reduced section comprises a bend to shorten a lateral distance between the spinal rod and the neighboring spinal rod.

84. The implant system of claim 67, wherein the first arm and the second arm each further comprise a tapered outer surface that is angled toward the threaded end.

85. The implant system of claim 67, wherein the spinal rod is positioned within the opening, and wherein a portion of the spinal rod is exposed from the opening.

86. The implant system of claim 67, wherein the body comprises a substantially U-shaped yoke having an axial length defined between a pair of outer edges, the yoke being formed between a top section and a bottom section, the top section comprising a first edge, the bottom section comprising a second edge, the first and second edges defining a width of the yoke, and wherein the first and second edges are curved such that the width of the yoke varies across the axial length of the yoke, and wherein the width of the yoke is greater at one of the outer edges of the yoke than at a location between the outer edges of the yoke.

87. The implant system of claim 67 wherein the first and second arms are deflectable to form a locking taper engagement with the spinal rod.

88. The implant system of claim 67, further comprising a slot in the connector between the receiving end and the fastening end, the slot enabling the first arm and the second arm to be deflected relative to one another.

89. The implant system of claim 67 wherein the fixation component further comprises a hook adapted to connect the fixation component to a spine element.

90. The implant system of claim 67 wherein the fastener is a nut.

91. A method of surgically implanting a spinal fixation system comprising:

connecting a fixation component to a portion of a spine, the fixation component comprising a body, the body comprising a cavity having an inner surface;

positioning a connector within the cavity, the connector comprising a receiving end that forms a substantially U-shaped opening having an open end, and wherein the connector is positioned within the cavity such that the inner surface of the cavity engages an outer surface of the receiving end;

positioning a spinal rod in the connector;

clamping the receiving end around the spinal rod to fixably secure the spinal rod within the opening.

92. The method of claim 91 wherein positioning a spinal rod in the connector comprises snapping the spinal rod into the opening.

93. The method of claim 91, wherein clamping the receiving end around the spinal rod comprises attaching a fastener to a fastener end of the connector and securing the fastener against the fixation component to compress the receiving end against the spinal rod and against the inner surface.

94. The method of claim 93, wherein the fastening end comprises a threaded shaft, wherein the fastener comprises a nut, and wherein securing the fastener against the fixation component comprises rotating the nut to couple the nut to the fixation component.

95. The connecting device of claim 7, further comprising a slot in the fastening end, the slot in communication with the borehole, wherein the slot is configured to allow the first arm and the second arm to flex so that the receiving end exerts a compressive force on the spinal rod during use.

96. The connecting device of claim 7, further comprising a fastener configured to engage the fastening end, wherein the fastener inhibits movement of the connector along the spinal rod during use.

97. The connecting device of claim 94, wherein the fastening end comprises a threaded shaft, and wherein the fastener comprises a nut.

98. The connecting device of claim 7, wherein the body is a hook.

99. The connecting device of claim 7, wherein the body is a bone screw.

100. The connecting device of claim 7, wherein the body is a transverse connector, the transverse connector configured to engage a second spinal rod positioned adjacent to the spinal rod.

101. The connecting device of claim 7, wherein the first arm and the second arm are configured to engage the spinal rod and surround more than half of a circumference of the spinal rod, but less than the complete circumference of the spinal rod.

102. The connector of claim 23, wherein the member comprises a slot in communication with the borehole, the slot configured to allowed the pair of deflectable arms to move towards each other.

103. The connector of claim 23, further comprising a nut configured to engage the member, and wherein the nut inhibits movement of the connector along the spinal rod when the nut is coupled to the member and tightened against the fixation component.

104. The connector of claim 23, wherein the fixation component comprises a transverse connector configured to engage a second spinal rod that positioned adjacent to the spinal rod.

105. The connector of claim 23, wherein the fixation component comprises a bone screw.

106. The connector of claim 23, wherein the fixation component comprises a hook.

* * * * *

UNITED STATES PATENT AND TRADEMARK OFFICE
CERTIFICATE OF CORRECTION

PATENT NO. : 6,132,430
DATED : October 17, 2000
INVENTOR(S) : Erik J. Wagner

It is certified that error appears in the above-identified patent and that said Letters Patent is hereby corrected as shown below:

Claim 7, col. 12, line 32, after "second end ", please insert --and --.

Signed and Sealed this

Twenty-second Day of May, 2001

Attest:

NICHOLAS P. GODICI

Attesting Officer

Acting Director of the United States Patent and Trademark Office